(12) United States Patent
Cauceglia et al.

(10) Patent No.: US 11,480,556 B1
(45) Date of Patent: Oct. 25, 2022

(54) METHOD AND APPARATUS FOR DETECTING TRACE AMOUNTS OF COPPER AND SILVER IN WATER

(71) Applicant: HF Scientific, LLC, Fort Myers, FL (US)

(72) Inventors: Dorian Cauceglia, Cape Coral, FL (US); Nicholas J. Pusateri, Cape Coral, FL (US)

(73) Assignee: HF Scientific, LLC, Fort Meyers, FL (US)

(*) Notice: Subject to any disclaimer, the term of this patent is extended or adjusted under 35 U.S.C. 154(b) by 368 days.

(21) Appl. No.: 16/859,073

(22) Filed: Apr. 27, 2020

(51) Int. Cl.
*G01N 33/18* (2006.01)
*G01N 21/78* (2006.01)
(Continued)

(52) U.S. Cl.
CPC .......... *G01N 33/1813* (2013.01); *B01L 3/502* (2013.01); *G01N 21/78* (2013.01);
(Continued)

(58) Field of Classification Search
CPC .... G01N 33/1813; G01N 21/78; G01N 31/22; B01L 3/502; B01L 2200/16;
(Continued)

(56) References Cited

U.S. PATENT DOCUMENTS 6,140,130 A * 10/2000 Salmen ................ G01N 21/643
422/62

OTHER PUBLICATIONS

Ahmed, M. Jamaluddin, et al., "A Rapid Spectrophotometric Method for the Determination of Trace Level Silver Using 1, 5-diphenylthiocarbazone in Aqueous Micellar Solutions," Apr. 17, 2014, in International Research Journal of Pure & Applied Chemistry 4(4): (pp. 468-485).

(Continued)

*Primary Examiner* — Jennifer Wecker
*Assistant Examiner* — Oyeleye Alexander Alabi
(74) *Attorney, Agent, or Firm* — Harris Beach PLLC; Laura W. Smalley

(57) ABSTRACT

Disclosed is a real-time method for detecting copper and silver in water in parts per billion. Total silver is detected by adding a 2% nitric acid solution to the sample; after ten minutes, adding a buffer solution comprising water, sodium bicarbonate, sodium carbonate and EDTA to the sample; adding an indicator comprising Cadion 2B, EtOH, and Triton X-100 to the sample; after one minute, reading the absorbance of the sample using a spectrophotometer with a target peak of 515 nm; and determining the silver concentration by comparing the absorbance of the sample to the absorbances of known silver standards. Total copper is detected by adding a 2% nitric acid solution to the sample; after ten minutes, adding a buffer/indicator solution to the sample, where the solution comprises water, sodium citrate dihydrate, hydroxal amine hydrochloride and bathocuproine disulfonate; after one minute, reading the absorbance of the sample using a spectrophotometer with a target peak of 480 nm; and determining the copper concentration by comparing the absorbance of the sample to the absorbances of known copper standards. A monitoring device for determining the level of copper or silver in a sample implements the disclosed methods.

14 Claims, 9 Drawing Sheets

(51) Int. Cl.
*G01N 31/22* (2006.01)
*B01L 3/00* (2006.01)

(52) U.S. Cl.
CPC .......... *G01N 31/22* (2013.01); *B01L 2200/16* (2013.01); *B01L 2300/041* (2013.01); *B01L 2300/06* (2013.01); *B01L 2300/0809* (2013.01); *B01L 2300/168* (2013.01); *B01L 2400/0475* (2013.01)

(58) Field of Classification Search
CPC .......... B01L 2300/041; B01L 2300/06; B01L 2300/0809; B01L 2300/168; B01L 2400/0475
See application file for complete search history.

(56) References Cited

OTHER PUBLICATIONS

Shah, Rupal, et al., "Spectrophotometric determination of microquantities of silver(I) using dithizone in the presence of cetyl trimethylammonium bromide", Nov. 1995, Indian Journal of Chemistry, vol. 34A (pp. 925-927).

Fu-Sheng, Wei, et al., "Spectrophotometric Determination of Silver with Cadion 2B and Triton X-100", 1982, Talanta, vol. 30, No. 3 (pp. 190-192).

Hach Company,"Silver", Doc316.53.01134, Jul. 2018, Edition 9 (pp. 1-8).

Mammadov, Polad R., et al., Simple and Rapid Spectrophotometric Determination Method for Trace Level of Silver Using 2,2'-DI (2,3,4-trihidroksifenilazo)Bifenil, 2018, New Materials, Compounds and Applications vol. 2, No. 2, (pp. 123-131).

Nikolov, Marian, et al., "Spectrophotometric Determination of Silver with Brilliant Green and its Application in Photographic Fixing Solutions," 2009, Ecological Chemistry and Engineering A, vol. 16, No. 4, (pp. 399-403).

Noll, C.A., et al., "Determination of Copper Ion by a Modified Sodium Diethylidithiocarbamate Procedure," Dec. 1952, Analytical Chemistry, (pp. 4, 4A and 1894-1895).

Dagnall, R. M., et al., "A Selective and Sensitive Colour Reaction for Silver," 1964, Talanta, vol. 11 (pp. 1533 to 1541).

* cited by examiner

RELATIVE INTENSITY VS. WAVELENGTH

METHOD AND APPARATUS FOR DETECTING TRACE AMOUNTS OF COPPER AND SILVER IN WATER

FIELD OF THE APPLICATION

This application relates to a method and apparatus for detecting trace amounts of copper and silver in water, specifically monitoring levels of copper and/or silver in real time.

BACKGROUND

Species of the bacteria *Legionella*, specifically *L. pneumophila*, can be fatal if contracted (as in Legionnaires' disease). In recent years, there has therefore been a growing need to eradicate *Legionella pneumophila* from premise plumbing systems in multi-level buildings such as hotels and hospitals. Research and case studies have shown that, in addition to chlorination, the use of copper-silver ionization can be beneficial in controlling certain bacteria species, including *L. pneumophila*. This method, aimed at the destruction of bacteria species, utilizes copper (Cu) and silver (Ag) ions to disrupt the cell walls of the bacteria, ultimately rendering the bacteria dead or unable to reproduce. CSI (Copper-Silver Ionization) is the process used to produce copper and silver ions in water and is a method growing in popularity for controlling/eradicating *Legionella pneumophila*.

There is little EPA/federal oversight regarding the detection methodology, schedule, and regulatory limits of *L. pneumophila*, so most commercial buildings will never test for *L. pneumophila* unless there is an immediate concern. However, there are established concentration limits for copper and silver in drinking water. While copper-silver ionization systems for building plumbing systems have been available for over 30 years, there has not been an effective method to monitor the levels of copper and silver in real time. Methods exist for detecting copper and silver in water, but these either require specialized field instrumentation and caustic chemicals, or require that samples be sent to a third party for analysis, a process which may make weeks.

The detection of *L. pneumophila* and the detection of copper and silver ions are both very difficult in real time. Bacteria detection involves common sample plating methods in a laboratory setting and may take up to seven days to produce results. Copper and silver detection involves sending out a water sample to a laboratory for ICP (Inductively Coupled Plasma) testing to determine concentration. The timing of the results can thus vary greatly. Several products are on the market for field testing of copper and silver in water, but they require the operator to take a sample and then perform the test using a handheld monitor, and the results may vary widely depending on the operator's sampling methodology and chemistry experience.

SUMMARY

An embodiment of a method for detecting total silver in a sample of water in parts per billion comprises: adding a 2% nitric acid solution to the sample; after ten minutes, adding a buffer solution with a pH of approximately 9.2 to the sample, wherein the buffer solution comprises water, sodium bicarbonate, sodium carbonate and EDTA; adding an indicator comprising Cadion 2B, EtOH, and Triton X-100 to the sample; after one minute, reading the absorbance of the sample using a spectrophotometer with an approximate target peak of 515 nm; and determining the concentration of silver by comparing the absorbance of the sample to the predetermined absorbances of known silver standards. Preferably, for each 3 mL of sample, approximately 50 µL of the nitric acid solution is added, 150 µL of the buffer solution is added, and 50 µL of the indicator is added.

Preferably, the components of the indicator solution are in essentially the proportions: 0.018 g of Cadion 2B, 22.5 mL of ethanol, and 2.5 mL of Triton X-100; and the components of the buffer solution are in essentially the proportions: 21 g of sodium bicarbonate and 4.2 g of sodium carbonate anhydrous made up to 250 mL with deionized water, and 0.438 g of EDTA with 1M NaOH as necessary to adjust pH to 9.2.

An embodiment of a method for detecting total copper in a sample of water in parts per billion comprises: adding a 2% nitric acid solution to the sample; after ten minutes, adding a buffer/indicator solution to the sample, wherein the buffer/indicator solution comprises water, sodium citrate dihydrate, hydroxal amine hydrochloride and bathocuproine disulfonate; after one minute, reading the absorbance of the sample using a spectrophotometer with an approximate target peak of 484 nm; and determining the concentration of copper by comparing the absorbance of the sample to the predetermined absorbances of known copper standards.

Preferably, for each 3 mL of sample, approximately 50 µL of the nitric acid solution is added and 150 µL of the buffer/indicator solution is added. Preferably, the components of the buffer/indicator solution are in essentially the proportions: 2 g sodium citrate dihydrate, 3 g hydroxal amine hydrochloride, and 0.03 g bathocuproine disulfonate dissolved in 25 mL of deionized water.

An embodiment of a monitoring device comprises: a case with a removable cover; a display panel located on or inside the case; a light transparent sample cell adapted to receive a fluid sample; an inlet line for receiving a fluid sample, the inlet line having a device for controlling water flow to the sample cell; at least four reagent containers for holding reagents; at least four pumps each adapted to pump a reagent from one of the reagent containers to the sample cell; at least one air pump; an optical board adapted to direct light through the sample cell, receive the light passing through the sample cell and generate a signal indicative of the contents of the fluid sample based upon the received light; an outlet line for draining the fluid sample from the sample cell, the outlet line having a device for controlling water flow from the sample cell; and a controller operatively connected to at least the display, the device for controlling water flow to the sample cell, the pumps, the optical board and the device for controlling water flow from the sample cell; wherein the optical board is connected to at least three light emitting diodes capable of operating separately, comprising a red LED, a 515 nm LED and a 480 nm LED, and wherein the controller receives data from the optical board and outputs to at least the display panel a measurement of parts per billion of silver or of copper by comparing the absorbance of the sample to the predetermined absorbances of known silver standards or to the predetermined absorbances of known copper standards.

Preferably, the output is determined for silver using a calibration curve where $Y=7836.1x^2-1383x-54.326$ where X is the absorbance and Y is the parts per billion of silver and the output is determined for copper by using a calibration curve where $Y=4702.2x-27.402$ where X is the absorbance and Y is the parts per billion of copper.

In an embodiment of a method for using the device disclosed above to determine the concentration of copper or silver in a fluid, the controller performs the steps comprising: taking an empty cell reading using the red LED; if the empty cell reading indicates the sample cell is empty, causing the device controlling water flow to the sample cell to fill the sample cell with a sample of liquid; taking a base absorbance reading; causing a first pump to inject the sample in the cuvette with a 2% nitric acid solution; causing the air pump to mix the sample; after ten minutes, if a determination of silver concentration is being made, causing (1) a second pump to inject the sample with a buffer solution with a pH of approximately 9.2 to the sample, wherein the buffer solution comprises water, sodium bicarbonate, sodium carbonate and EDTA; and then (2) a third pump to inject the sample with an indicator comprising Cadion 2B, EtOH, and Triton X-100; or after ten minutes, if a determination of copper concentration is being made, causing a fourth pump to inject the sample with a buffer/indicator solution, wherein the buffer/indicator solution comprises water, sodium citrate dihydrate, hydroxal amine hydrochloride and bathocuproine disulfonate; causing the air pump to mix the sample; and after one minute, taking an absorbance reading using the 515 nm LED for silver or the 480 LED for copper.

Preferably, the output is determined for silver using a calibration curve where $Y=7836.1x^2-1383x-54.326$ where X is the absorbance and Y is the parts per billion of silver and the output is determined for copper by using a calibration curve where $Y=4702.2x-27.402$ where X is the absorbance and Y is the parts per billion of copper. Preferably, when the concentration of silver is being determined, for each 3 mL of sample, approximately 50 μL of the nitric acid solution is added, 150 μL of the buffer solution is added, and 50 μL of the indicator is added. Preferably, the components of the indicator solution are in essentially the proportions: 0.018 g of Cadion 2B, 22.5 mL of ethanol, and 2.5 mL of Triton X-100; and (2) the components of the buffer solution are in essentially the proportions: 21 g of sodium bicarbonate and 4.2 g of sodium carbonate anhydrous made up to 250 mL with deionized water, and 0.438 g of EDTA with 1M NaOH as necessary to adjust pH to 9.2.

DETAILED DESCRIPTION

Figure 1:
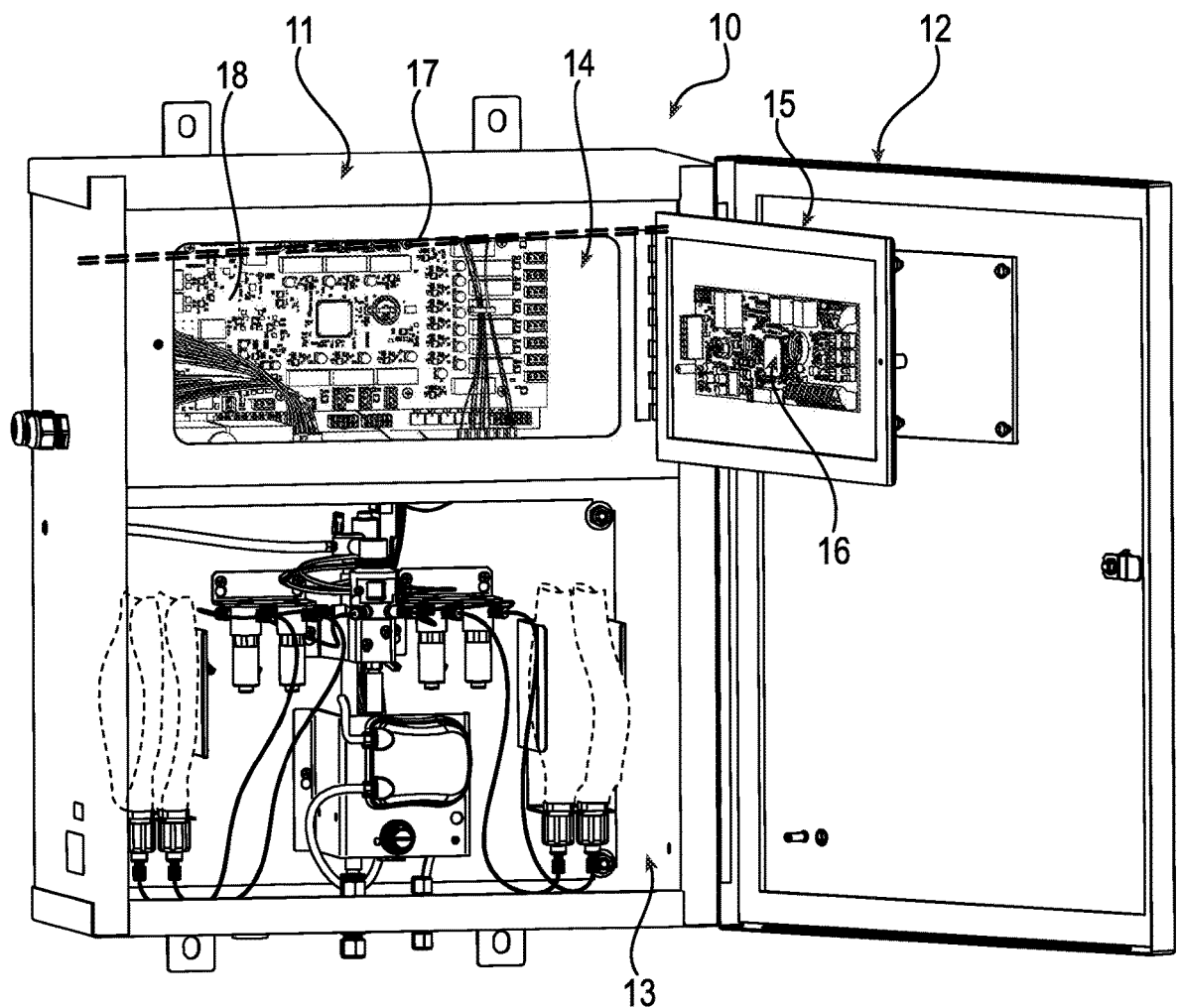
FIG. 1 shows an exemplary embodiment of the disclosed monitor.

An embodiment of the disclosed method allows the detection of copper and silver with an acceptable degree of accuracy down to 50 ppb of silver and 200 ppb of copper. The method involves the delivery of specially-developed chemical reagents to a given water sample, which will produce a detectable color change in the presence of copper or silver. The color change is detected as an absorbance value using a highly sensitive optical system. The absorbance output is converted to a parts per billion (ppb) reading. The method may also be used in an on-line real-time monitor.

Beer's Law is the fundamental spectrophotometry principle in the disclosed method of colorimetric detection. Beer's Law states: $A=\varepsilon\ b\ c$ where:

A is absorbance (no units)

E is the molar absorptivity coefficient, stated in $L\ mol^{-1}\ cm^{-1}$ b is the path length of the sample, usually measured in cm c is the concentration of the compound in solution, stated as $mol\ L^{-1}$.

According to this equation, the concentration of a sample (in mol/L) is directly proportional to its absorbance, as measured on a spectrophotometer. Using Beer's Law in the disclosed method allows the absorption of a known chemical (i.e., silver has its highest absorbance at 515 nm) to be translated into the concentration of that chemical.

Chemistry for Detecting Trace Amounts of Silver and Copper

Methods of detecting trace amounts of silver are known. See Fu-Sheng and Yang, *Spectrophometric Determination of Silver with Cadion 2B and Triton X-10*, which is incorporated by reference. Fu-Sheng describes the use of Triton X-100 as a suspension agent and Cadion 2B as an indicator. The Cadion 2B and silver complex form a dark red-violet complex at pH 9.2 in the presence of Triton X-100, with an absorption maximum of 565 nm.

Methods of detecting trace amounts of copper are known. See C. A. Noll, Lorraine Betz, *Determination of Copper Ion by Modified Sodium Diethyldithiocarbamate Procedure*, Analytical Chemistry 24, 12, 1894-1895 (1952), which is incorporated by reference in its entirety. Noll describes the use of a sodium diethyldithiocarbamate solution and an ammonium hydroxide reagent to detect copper. The solution produces a yellow color.

The methods described above were insufficient to detect trace elements of silver and copper, particularly down to 50 ppb silver and 200 ppb copper, in water.

Achieving the detection of total metals required, among other things, a ten-minute acid digestion within the sample cell prior to the addition of the applicable detection chemistry. The acid used for digestion is 50 μL of a 2% Nitric acid (CAS 7697-37-2) solution per 3 mL of sample. The process needed to regulate the pH of the sample without significantly diluting the sample. With respect to the detection of silver, Cadion 2B (indicator) is shown to have a working range of pH 9.1-9.5 with an optimal working pH of 9.3 for best results (highest resolution). The acid digestion step, however, must take place at below pH 2.0 to be effective. Therefore, a buffer had to be formulated that was strong enough to bring 3.05 mL of digested sample from a pH of less than 2.0 to a pH of at least 9.1 while using as little volume as possible.

An example of the formula used in the detection of total silver is:

Indicator solution: 0.018 g of Cadion 2B (CAS 6708-61-8) in 22.5 mL of EtOH, stir in 2.5 mL with Triton X-100 (CAS 9002-93-1).

Buffer solution: (A) Silver Buffer: 21 g of sodium bicarbonate (CAS 144-55-8) and 4.2 g of sodium carbonate anhydrous (CAS 497-19-8) dissolved in deionized water and made up to 250 mL; (B) Silver B-Solution: While stirring add 0.438 g of EDTA (CAS 6381-92-6) in 20 mL of (A) until fully dissolved. Use 1M NaOH adjust pH to 9.2.

All solutions described here dissolve quickly with only agitation (stir plate), no heat required.

With respect to the detection of total copper, bathocuproine disulfonate (indicator) is shown to have a working range of pH 4.3-4.6 with an optimal working pH closer to 4.3 for best results (highest resolution). The acid digestion has to be below pH 2.0 to be effective. Therefore, a buffer had to be formulated that was strong enough to bring 3.05 mL of digested sample from a pH of less than 2.0 to a pH of at least 4.3 while using as little volume as possible.

An example of the formula used in the detection of total copper is:

Combined buffer/indicator solution: 2 g sodium citrate dihydrate (CAS 6132-04-3), 3 g hydroxal amine hydrochloride (CAS 5470-11-1), and 0.03 g bathocuproine disulfonate (CAS 52698-84-7) dissolved in 25 mL of deionized water.

This solution dissolves quickly with only agitation (stir plate), no heat required.

The disclosed formulae were verified as follows. The components were combined in calculated amounts and complete solubility was verified. The pH of the reagent produced was tested to make sure it was in the desired range, i.e. target pH 4.3-4.6 for the copper indicator.

A known silver or copper standard (i.e., Sigma Aldrich concentrated Cu at 1000 ppm+/−4 ppm) was then used and proper, accurate dilutions were made to reach the desired concentration, using precision glassware (pipettes from 100 mL to 0.5 mL) and micropipettes (1 mL to 1 μL) and proper pipetting techniques. The dilutions were made using the formula $C_1V_1=C_2V_2$.

For Silver detection: 50 μL 2% Nitric acid was added to a 3 mL sample, mixed, and allowed to sit ten minutes for acid digestion. Then, 150 μL of the buffer was added to the solution, and the solution was mixed. Thereafter, 50 μL of the indicator was added to the solution, which was mixed again. The solution was allowed to sit for one minute for color development. The absorbance of the color produced was read on a Perkin Elmer 365 UV/Vis spectrophotometer at the appropriate wavelength (target peak of 515 nm for Ag chemistry absorbance).

For copper detection: 50 μL 2% Nitric acid was added to a 3 mL sample, mixed, and allowed to sit ten minutes for acid digestion. Then, 250 μL of the buffer/indicator solution was added to the solution and the solution was mixed. The solution was allowed to sit for one minute for color development. The absorbance of the color produced was read on a Perkin Elmer 365 UV/Vis spectrophotometer at the appropriate wavelength (target peak of 480 nm for copper chemistry absorbance).

The pH of the resulting product (3 mL sample+reagent) was read to ensure the chemistry was still acting within the desired range, i.e. target pH 4.3-4.6 for the Cu indicator. The steps above, starting at using a known silver or copper standard, were repeated for several different concentrations of standard through the desired range (for example, test concentrations of 200 ppb, 500 ppb, 1500 ppb and 2000 ppb Cu). The delta between absorbance readings, particularly at the high and low end of the desired range, was observed—i.e., the difference between 0 ppb and 200 ppb, or the difference between 1800 ppb and 2000 ppb. A higher delta indicates better resolution.

Then, the method was tested again using the steps above, but instead of using only the standard in question (e.g., 500 ppb Cu), a combined standard was used with a known value of the other component (e.g., a solution of 500 ppb Cu and 200 ppb Ag). This testing verified that there is no interference between the two chemistries or the two metals in the same solution.

Below in Table 1 is the spectrophotometer comparison data for silver.

TABLE 1

| Sample | Wavelength-515 nm |
| --- | --- |
| Ag V4.6 DI water | 0.1199 |
| Ag V4.6 25 ppb | 0.1311 |
| Ag V4.6 50 ppb | 0.1413 |
| Ag V4.6 75 ppb | 0.1579 |
| Ag V4.6 100 ppb | 0.1787 |
| Ag V4.6 125 ppb | 0.2058 |
| Ag V4.6 150 ppb | 0.217 |
| Ag V4.6 175 ppb | 0.2387 |
| Ag V4.6 200 ppb | 0.2474 |
| Ag V4.6 225 ppb | 0.2602 |
| Ag V4.6 250 ppb | 0.2772 |

Below in Table 2 is the spectrophotometer comparison data for copper.

TABLE 2

| Sample | Wavelength-480 nm |
| --- | --- |
| Cu V1.7 DI water | 0.0036 |
| Cu V1.7 200 ppb | 0.0368 |
| Cu V1.7 400 ppb | 0.0735 |
| Cu V1.7 600 ppb | 0.1138 |
| Cu V1.7 800 ppb | 0.1537 |
| Cu V1.7 1000 ppb | 0.1879 |
| Cu V1.7 1200 ppb | 0.2298 |
| Cu V1.7 1400 ppb | 0.2614 |
| Cu V1.7 1600 ppb | 0.3013 |
| Cu V1.7 1800 ppb | 0.3354 |
| Cu V1.7 2000 ppb | 0.3726 |

Next, the above process was used to determine whether samples produced by a copper-silver ionization system produced similar, acceptable results. In using the method, adjustments to the chemistry may be necessary depending on the testing results obtained during the verification phase. Any sufficiently accurate method of determining the absorbance may be used, including a colorimeter.

Monitoring System

The above-disclosed method may be incorporated in an online instrument platform to be used in conjunction with, for example, a commercial copper silver ionization system. Such systems may be portable units on carts or fixed rack units that connect to an existing plumbing or water delivery system. As shown in FIG. 1, an exemplary instrument or monitor 10 includes a case 11 with a removable front cover 12. The front cover 12 defines a window 13 to allow operator monitoring and access for consumable replacements and services. The monitor may have hardware security that would prevent the end user from tampering with the instrument or programmed settings.

The case may have a separate interior compartment 14 with a removable or movable cover 15. The cover 15 may have a display 16 (shown from the back). Electrical power is provided to the monitor 10 and to the various electrical and electronic components thereof through a connector 17 that extends through the case 11 as partially shown in FIG.

1. The separate interior compartment may house an electronic controller (i.e., computer processor/board) 18 that is operatively connected to the various components of the monitor 10. The controller and/or the monitor may also be connected to an alarm system.

Figure 2:
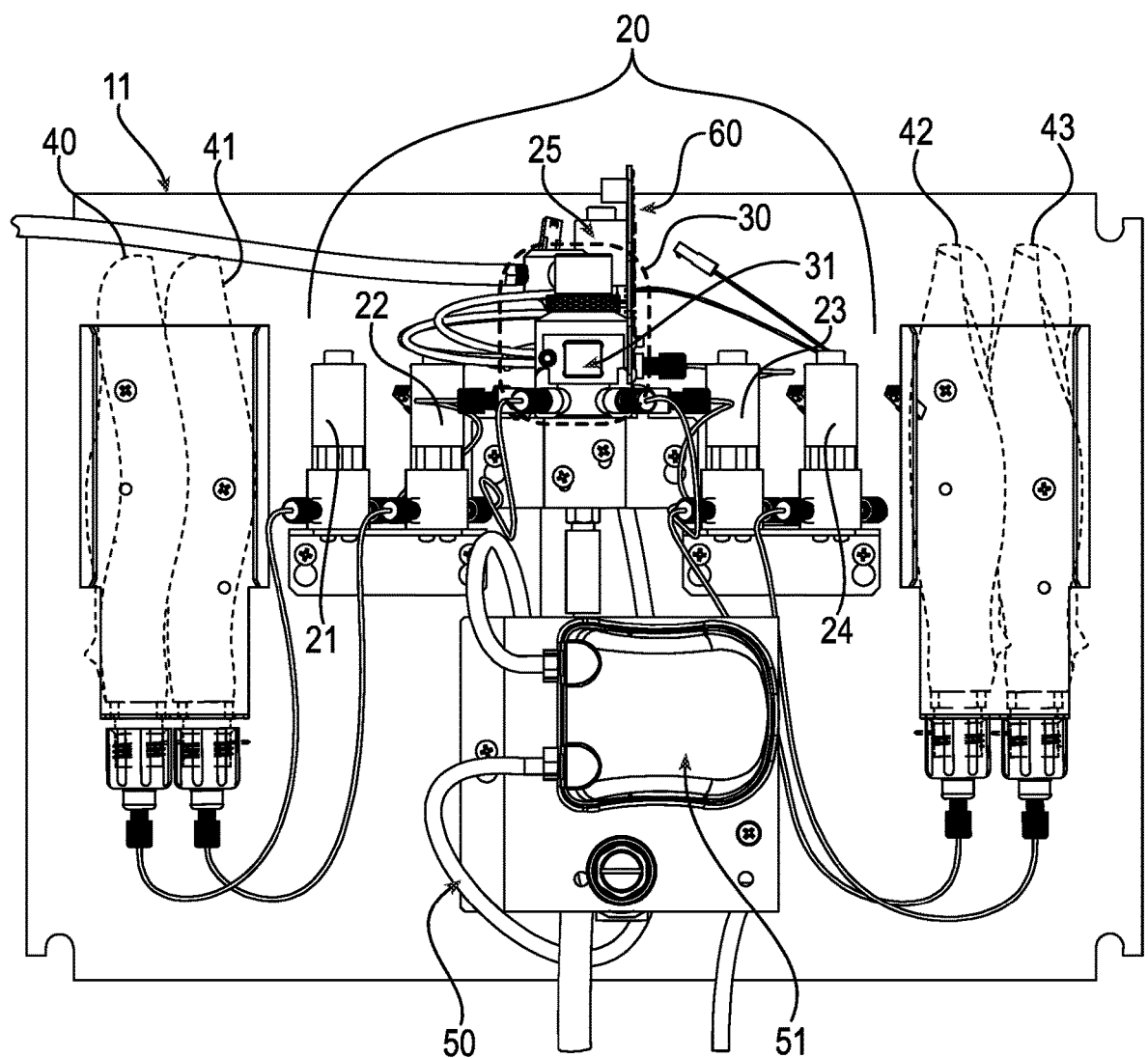
FIG. 2 shows an exemplary embodiment of the interior of the disclosed monitor.

As shown in FIG. 2, the interior of the case 11 contains a pump assembly 20, including four reagent pumps (21, 22, 23 and 24) and an air pump 25, arranged on an optical block 30. In an exemplary embodiment, the pumps are solenoid. The optical block 30 holds a sample cell 31. The term "sample cell" is meant to refer broadly to a container for holding the liquid sample. Preferably, the sample cell should be covered to prevent exterior light from affecting the results. Preferably, the sample cell will have a path length of one centimeter or, more preferably, three centimeters. The reagent pumps transfer the reagents from reagent containers/bags (40, 41, 42, and 43) to the sample cell. The monitor 10 includes an inlet line 50 for receiving a water sample, and a peristaltic pump 51 for controlling flow of the water sample to the sample cell 31 for testing. A drain valve, not pictured, controls the flow from the sample cell to a drain line after testing has been completed. According to one exemplary embodiment, valves may additionally control the flow into and out of the sample cell.

Figure 3:
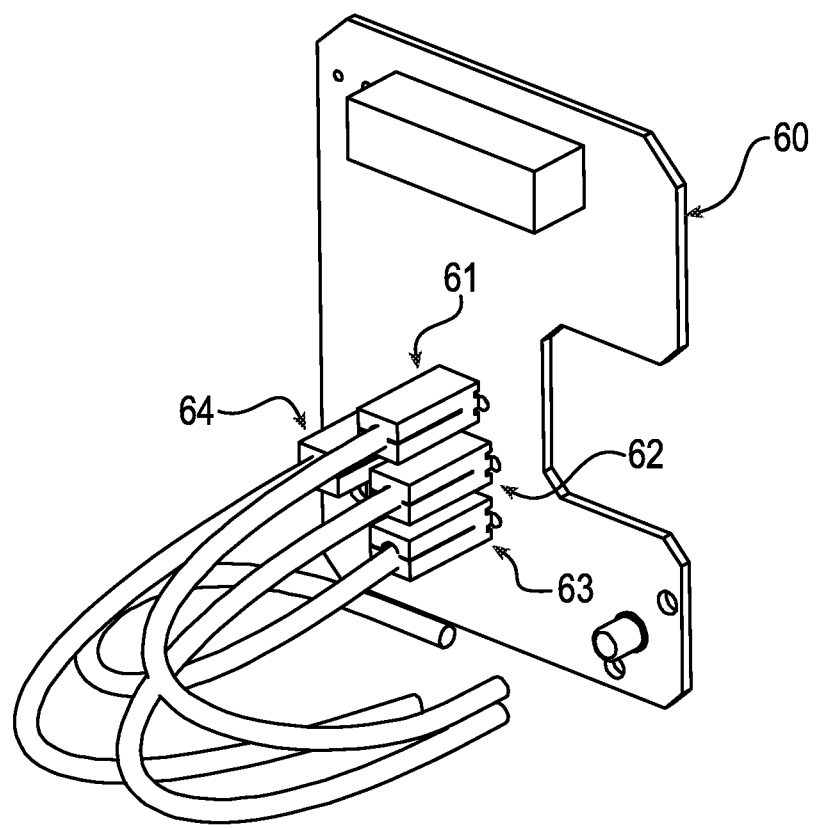
FIG. 3 shows an optical board with four light pipes containing LEDs.
Figure 4:
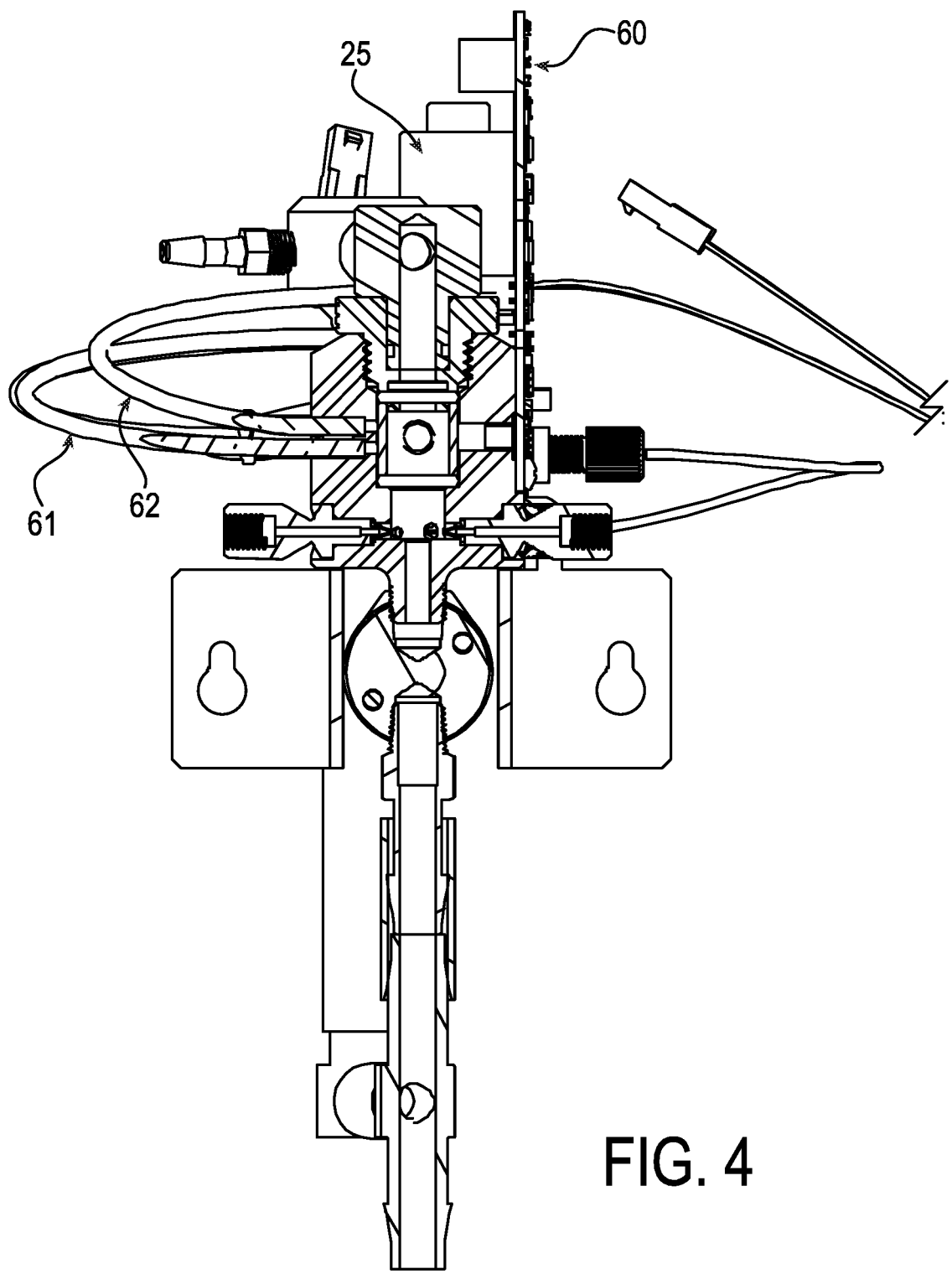
FIG. 4 shows the side view of the optical board inside the monitor.

An optical board 60 is connected to or adjacent to the optical block 30. The optical board 60 is shown more clearly in FIGS. 3 and 4. FIG. 3 shows the optical board 60 with four light pipes containing LEDs (61, 62, 63, and 64). The light pipes may be rigid or, more preferably, flexible. The LEDs include red, blue and green LEDs. The optical board controls the LEDs and collects the raw data from the sample testing. Another embodiment of the disclosed devices uses a colorimeter.

The controller 18 is programmed to control: delivery of the water sample to the sample cell 31 using the pump 51; delivery of the reagents to the sample cell using one or more of the reagent pumps, testing of the sample by the LEDs and optical board; and draining of the water sample from the sample cell after testing. Signals representing photometric measurements provided by the LEDs are collected and transmitted by the optical board to the controller, which then displays the results on the display panel 16. Although not viewable in the drawings, the monitor may also have a memory or SD card (in addition to output on the display) for data retrieval. The controller may, preferably, control the copper-silver ionization system by outputting signals either through a cable or similar means or remotely.

Calibration curves were generated for a prototype of a monitor as described above. Multiple real-world water samples generated by copper/silver ionization were gathered and the absorbance values for those samples were determined. The concentration of silver and copper in the samples was calculated in parts per billion.

A sample was fed into the prototype monitor under normal system and software conditions. The controller caused the monitor to perform: (1) a sample wash of two peristaltic pump cycles; (2) an empty cell reading, known as a level detect reading, using a red LED that will be detected by the photodiode at a different angle due to water refraction and will determine if the sample cell is empty or is filled with water; (3) a sample cell reading, using the same red LED and method described in the previous step, after the cell is full of sample; (4) a dark reading, known as a zero reading, which is a base absorbance reading that will be subtracted from the final absorbance reading to obtain the true absorbance value. This zero reading is meant to account for ambient or other light interference; (5) injection of 50 µL of 2% Nitric acid (2 pump pulses); (6) an air mix that uses ~50 pulses of the free (air) pump to create bubbles to properly mix the sample inside the cell; (7) an idle period of 10 minutes for the acid digestion process to take place; (8) the addition of appropriate chemical reagents (depending on which metal is being tested for) and additional air mixing; and (9) a 1-minute color development period. Then, the absorbance of the color created by the chemical reaction in the sample cell is read and optionally recorded on a microSD card with a date/time stamp. The effluent waste from the prototype monitor was captured and associated with the recorded absorbance. The waste sample was then tested for absorbance and pH using a Perkin Elmer 365 and the Oakton Ion 700 pH meter, respectively. The process was repeated with multiple samples.

The prototype monitor outputted acceptable samples that matched (in color, absorbance, & pH value) the same samples tested using the bench chemistry (for example, Tables 1 and 2). Although the optical systems differ between the prototype monitor and the Perkin Elmer, the data had acceptable delta values between samples within each instrument. If the outputs from the prototype monitor had not been acceptable, the number of reagent pump pulses would have been adjusted to match the bench chemistry outputs. It is recognized that, depending on how the method is implemented, optimization of the disclosed method may be necessary.

Once the monitor output is acceptable, consistent, and closely matches the bench examples in color, absorbance, and pH, the optimization process is complete. Next, a calibration curve using the prototype monitor's absorbance values as inputs (X) was generated, and it was verified that that the absorbance values returned acceptable concentration (ppb) values (Y). The verification entailed: (1) water samples were prepared using a copper-silver ionization system, which were read on the spectrophotometer and this data was compared to the data previously collected, for example, as outlined in Tables 1 and 2; (2) the samples were then read on the prototype monitor; (3) the absorbance values recorded from the monitor and the calculated concentration values from the data in Tables 1 and 2 were used to build a calibration curve; (4) the current version of the curve was input into the monitor's software; (5) the prototype monitor was fed the same (or similar) samples; (6) it was verified that the known sample inputs (X) generated acceptable parts per billion concentration values (Y) on the prototype monitor as compared to the bench chemistry outlined in Tables 1 and 2; (7) and the percent error associated with the new curve was calculated which indicate the error/accuracy for the instrument.

Figure 5:
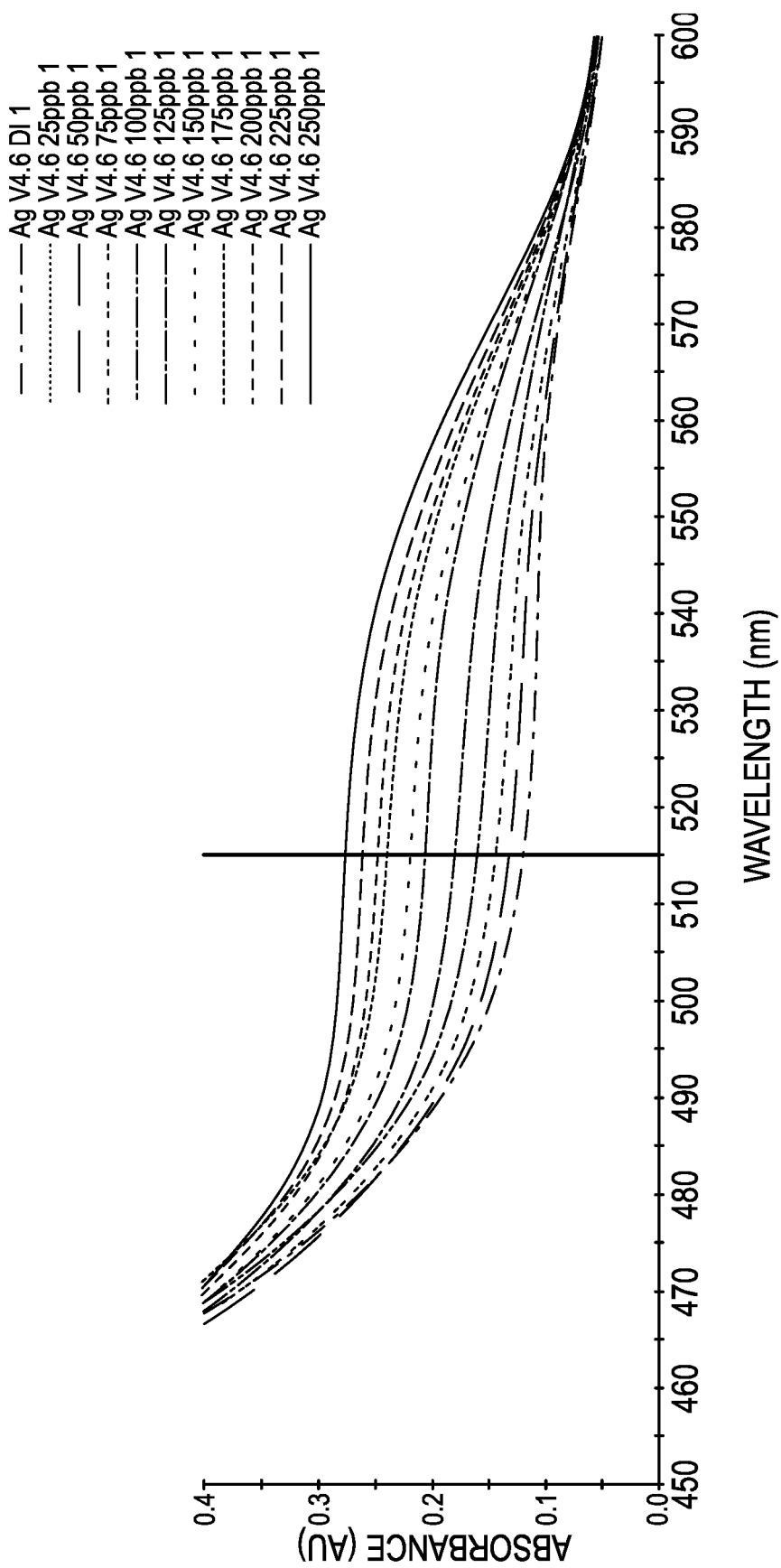
FIG. 5 is a spectrophotometer graph depicting silver chemistry absorbance.
Figure 6:
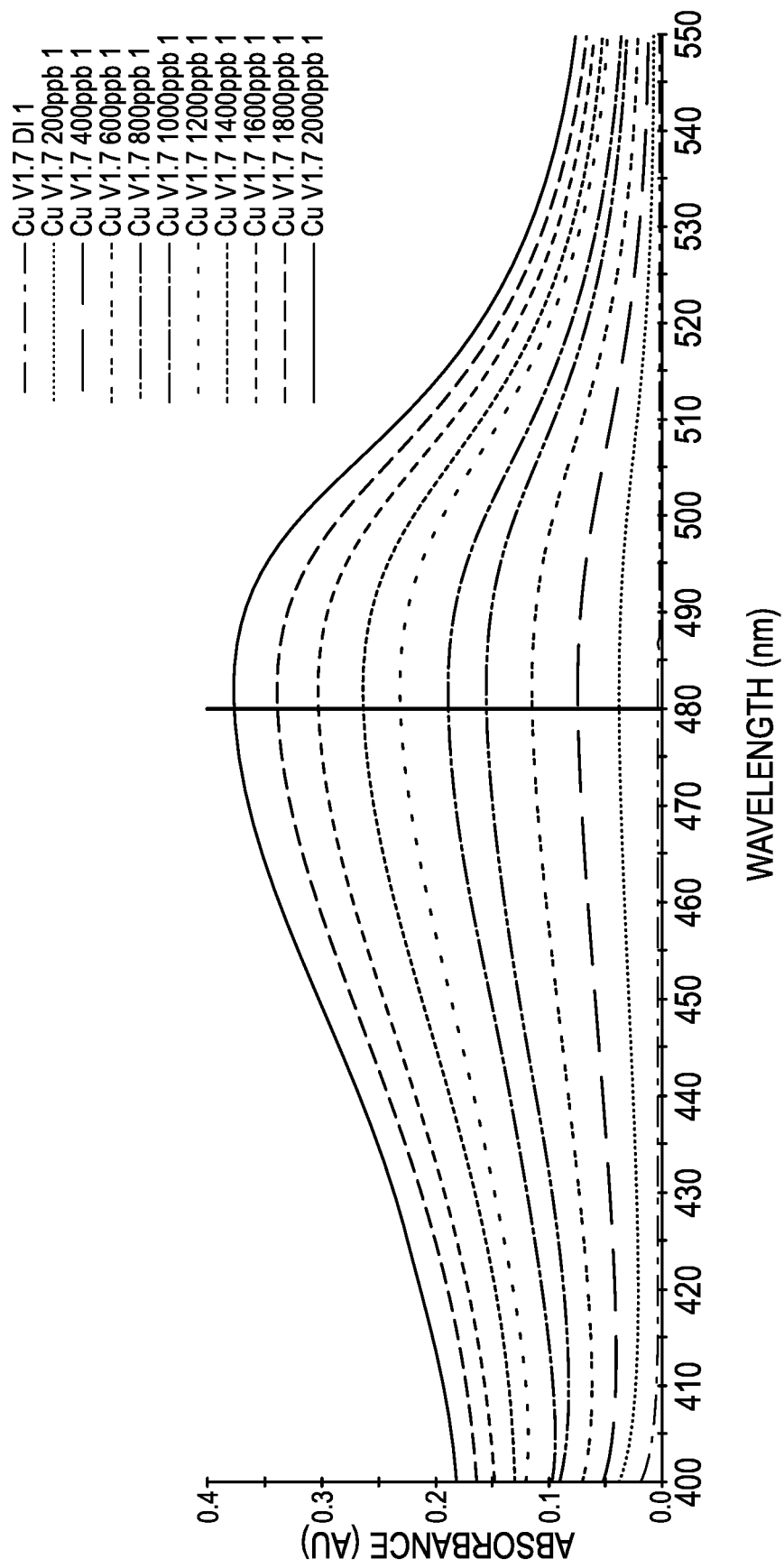
FIG. 6 is a spectrophotometer graph depicting copper chemistry absorbance.

The calibration curves presented as FIGS. 5 and 6 were created using the instrument optimization, sample generation, and comparison methodology described above. The below settings were found to most closely mimic the bench chemistry procedures described above based on the effluent sample pH and visual color output. These settings were developed using reagent pumps calibrated to 25 µL+/−2.5 µL. Settings used were: (1) 9 pulses of Ag buffer reagent pump; (2) 3 pulses Ag indicator reagent pump; (3) 10 pulses Cu indicator reagent pump; and (4) 2 pulses $HNO_3$ reagent pump.

The above process generated the following calibration curve for silver: $Y=7836.1x^2-1383x-54.326$. $R^2=0.9493$.

Table 1 shows the spectrophotometer comparison (chemistry validation) data used as basis for the silver calibration curve. FIG. 5 displays the peak chemical absorbance at wavelength 515 nm, and gives a delta between 0 ppb and 250 ppb silver of 0.1573 absorbance units.

The above process generated the following calibration curve for copper: Y=4707.2x−27.402. $R^2$=0.9973

FIG. 6 displays the peak chemical absorbance at wavelength 480 nm, and gives a delta between 0 ppb and 2000 ppb copper of 0.3690 absorbance units.

LED Selection

At noted above, the method works by colorimetric detection. Because the chemistry works by colorimetric detection, an appropriate LED must be used in this method. The LED should have a wavelength that best absorbs the color produced by the chemistry.

Figure 7:
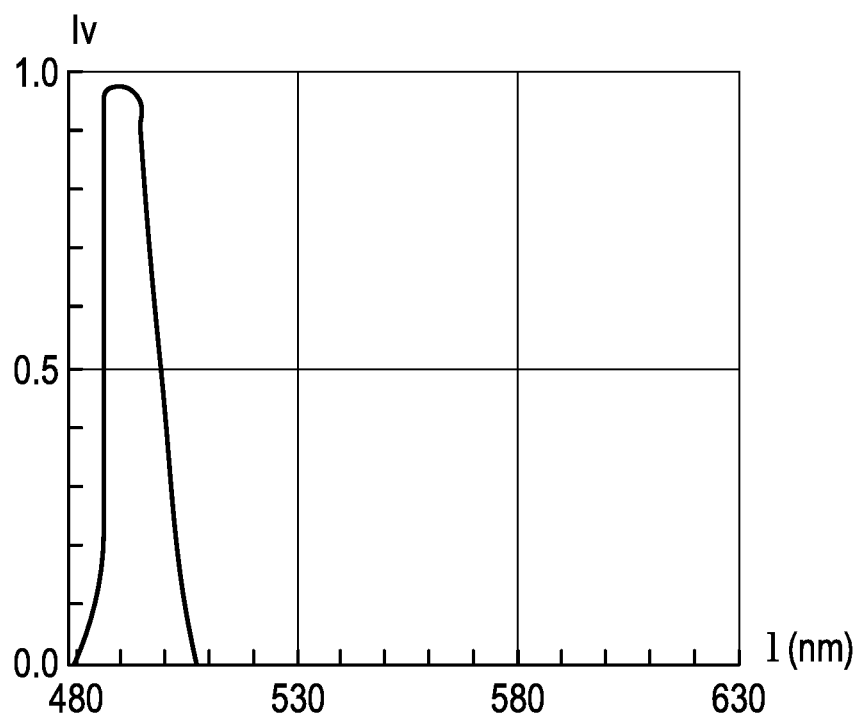
FIG. 7 is the peak wavelength for a light emitting diode (LED) used in the detection of silver ions.
Figure 8:
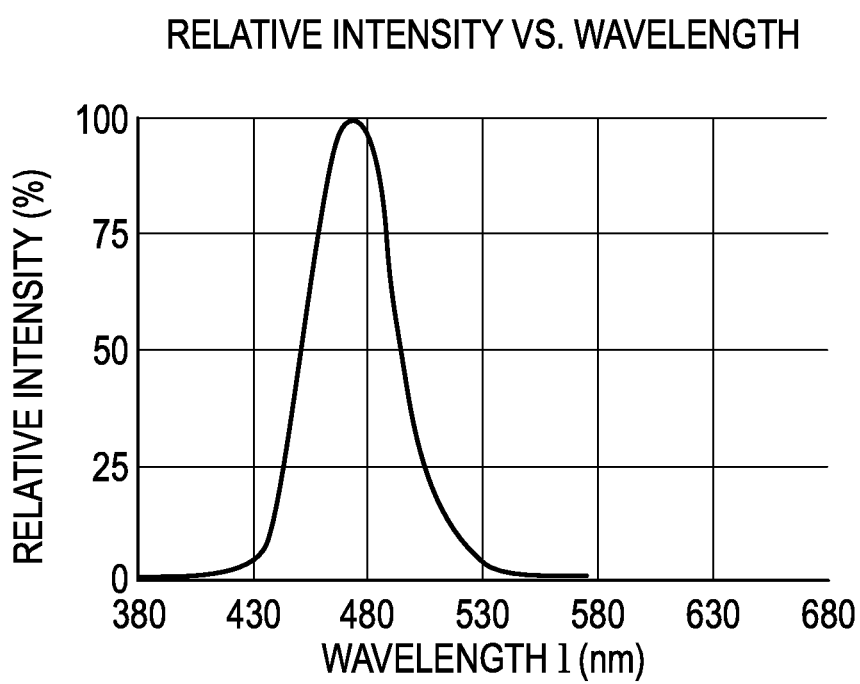
FIG. 8 shows the peak wavelength for an LED used in the detection of copper ions.

A PC-operated Ocean Optics spectrophotometer was used to measure the exact wavelength peak and breadth for several LEDs. In the case of silver, which produces a yellow/red color, a green 515 nm LED was selected for detection. The LED should not be too bright and should have the correct dominant peaks. An example of such an LED is a Bivar LED, Manufacturer PN: 749-3UTC-F. FIG. 7 is a graph showing the peak wavelength (in nm) of the Bivar LED. In the case of Cu, which produces an orange color, a blue LED near 484 nm was selected for detection. An example of such an LED is from the Visual Communications Company (sold by Digikey). FIG. 8 is a graph showing the peak wavelength (in nm) of the Visual Communications Company LED.

Figure 9:
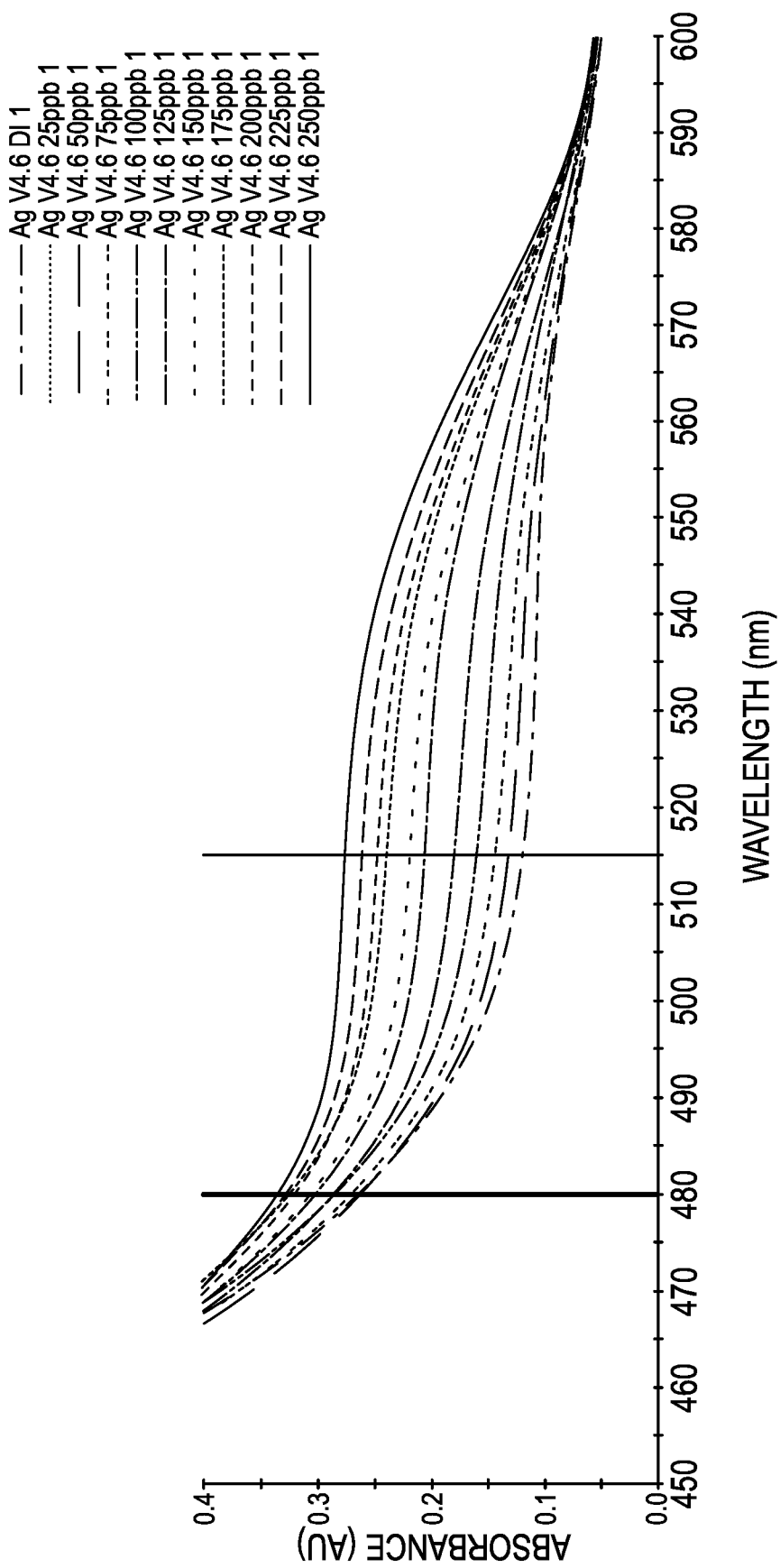
FIG. 9 is spectrophotometer graph depicting the full spectrum of silver chemistry absorbance.

The above calibration curves (FIGS. 5 and 6) were generated after the correction of peak interferences. Due to limitations of current circuit design, both the green and blue LEDs ran simultaneously. The silver indicator's natural color absorbs within 480 nm (see FIG. 6), which is the wavelength used to detect the copper chemistry. The absorption signal at 480 nm is greater than the signal at a 515 nm measurement. Therefore, the presence of the illuminated 480 nm LED presented a positive interference when measuring silver. Therefore, the blue LED wire must be cut when taking silver absorbance readings. FIG. 9 shows the full spectrum of the silver chemistry absorbance.

Figure 10:
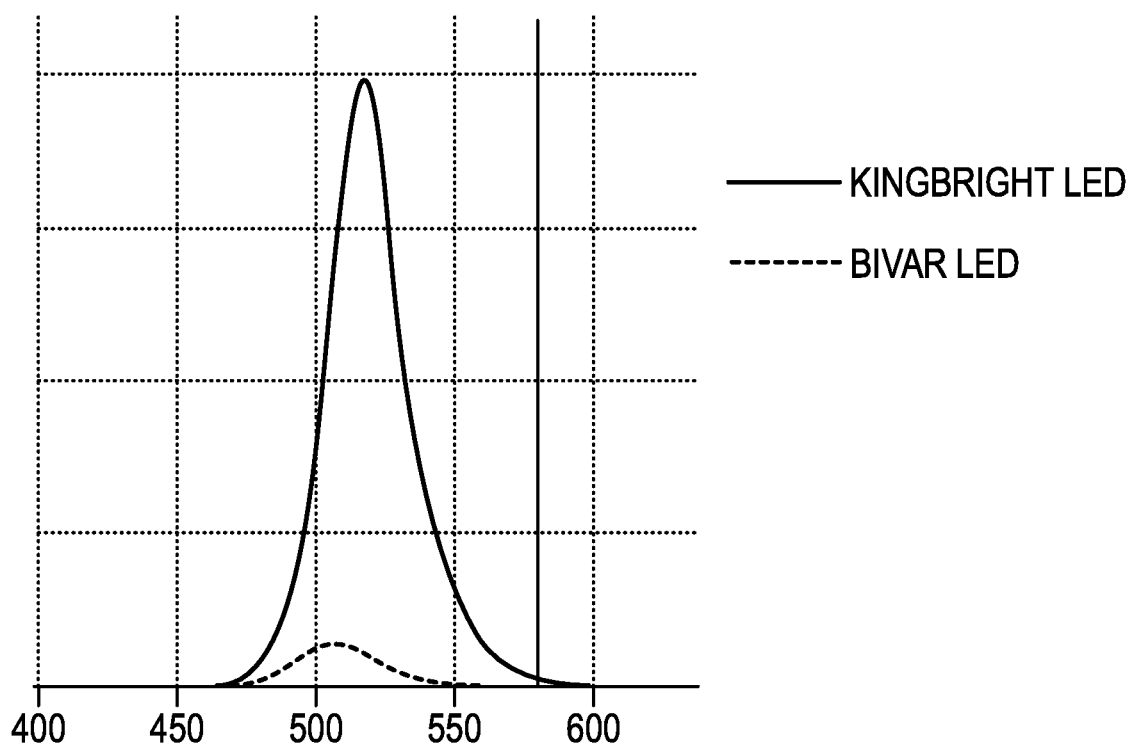
FIG. 10 is a graph showing the peak wavelength of a Bivar LED.

Based on FIG. 9, the silver chemistry absorbance spans from approximately 500 to 530 nm with the peak at 515 nm. Therefore, preferably, an LED used in the method will have the bandwidth and peak wavelength of the Bivar LED, or a narrower bandwidth, with a dominant peak between 515 and 530 nm. FIG. 10 displays the peak wavelength of the Pocket Photometer (Bivar) LED.

It will be appreciated that variants of the above-disclosed device and method and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for detecting total silver in a sample of water in parts per billion, the method comprising:
    Adding a 2% nitric acid solution to the sample;
    After ten minutes, adding a buffer solution with a pH of approximately 9.2 to the sample, wherein the buffer solution comprises water, sodium bicarbonate, sodium carbonate and EDTA;
    Adding an indicator comprising Cadion 2B, EtOH, and Triton X-100 to the sample;
    After one minute, reading the absorbance of the sample using a spectrophotometer with an approximate target peak of 515 nm; and
    Determining the concentration of silver by comparing the absorbance of the sample to the predetermined absorbances of known silver standards.

2. The method of claim 1 wherein for each 3 mL of sample, approximately 50 μL of the nitric acid solution is added, 150 μL of the buffer solution is added, and 50 μL of the indicator is added.

3. The method of claim 2 wherein: (1) the components of the indicator solution are in essentially the proportions: 0.018 g of Cadion 2B, 22.5 mL of ethanol, and 2.5 mL of Triton X-100; and (2) the components of the buffer solution are in essentially the proportions: 21 g of sodium bicarbonate and 4.2 g of sodium carbonate anhydrous made up to 250 mL with deionized water, and 0.438 g of EDTA with 1M NaOH as necessary to adjust pH to 9.2.

4. A method for detecting total copper in a sample of water in parts per billion, the method comprising:
    Adding a 2% nitric acid solution to the sample;
    After ten minutes, adding a buffer/indicator solution to the sample, wherein the buffer/indicator solution comprises water, sodium citrate dihydrate, hydroxal amine hydrochloride and bathocuproine disulfonate;
    After one minute, reading the absorbance of the sample using a spectrophotometer with an approximate target peak of 484 nm; and
    Determining the concentration of copper by comparing the absorbance of the sample to the predetermined absorbances of known copper standards.

5. The method of claim 4 wherein, for each 3 mL of sample, approximately 50 μL of the nitric acid solution is added and 150 μL of the buffer/indicator solution is added.

6. The method of claim 5 wherein the components of the buffer/indicator solution are in essentially the proportions: 2 g sodium citrate dihydrate, 3 g hydroxal amine hydrochloride, and 0.03 g bathocuproine disulfonate dissolved in 25 mL of deionized water.

7. A monitoring device comprising,
    a case with a removable cover;
    a display panel located on or inside the case;
    a light transparent sample cell adapted to receive a fluid sample;
    an inlet line for receiving a fluid sample, the inlet line having a device for controlling water flow to the sample cell;
    at least four reagent containers for holding reagents;
    at least four pumps each adapted to pump a reagent from one of the reagent containers to the sample cell;
    at least one air pump;
    an optical board adapted to direct light through the sample cell, receive the light passing through the sample cell and generate a signal indicative of the contents of the fluid sample based upon the received light;
    an outlet line for draining the fluid sample from the sample cell, the outlet line having a device for controlling water flow from the sample cell; and
    a controller operatively connected to at least the display, the device for controlling water flow to the sample cell, the pumps, the optical board and the device for controlling water flow from the sample cell;
    wherein the optical board is connected to at least three light emitting diodes capable of operating separately, comprising a red LED, a 515 nm LED and a 480 nm LED, and
    wherein the controller receives data from the optical board and outputs to at least the display panel a measurement of parts per billion of silver or of copper, and wherein the controller is programmed to compare comparing the absorbance of the sample to the predetermined absorbances of known silver standards or to the predetermined absorbances of known copper standards; and wherein the controller is programmed to perform the following steps: after ten minutes, if a determination of silver concentration is being made, causing (1) a second pump to inject the sample with a buffer solution with a pH of approximately 9.2 to the sample, wherein the buffer solution comprises water, sodium bicarbonate, sodium carbonate and EDTA; and then (2) a third pump to inject the sample with an indicator comprising Cadion 2B, EtOH, and Triton X-100;

or after ten minutes, if a determination of copper concentration is being made, causing a fourth pump to inject the sample with a buffer/indicator solution, wherein the buffer/indicator solution comprises water, sodium citrate dihydrate, hydroxal amine hydrochloride and bathocuproine disulfonate;

and after one minute, taking an absorbance reading using the 515 nm LED for silver or the 480 LED for copper.

8. The device of claim 7 wherein the output is determined for silver using a calibration curve where $Y=7836.1x^2-1383x-54.326$ where X is the absorbance and Y is the parts per billion of silver and the output is determined for copper by using a calibration curve where $Y=4702.2x-27.402$ where X is the absorbance and Y is the parts per billion of copper.

9. A method for using the device of claim 7 to determine the concentration of copper or silver in a fluid, wherein the controller performs the steps comprising:

taking an empty cell reading using the red LED;

if the empty cell reading indicates the sample cell is empty, causing the device controlling water flow to the sample cell to fill the sample cell with a sample of liquid; taking a base absorbance reading;

causing a first pump to inject the sample in the cuvette with a 2% nitric acid solution;

causing the air pump to mix the sample; and causing the air pump to mix the sample.

10. The method of claim 9 wherein the output is determined for silver using a calibration curve where $Y=7836.1x^2-1383x-54.326$ where X is the absorbance and Y is the parts per billion of silver and the output is determined for copper by using a calibration curve where $Y=4702.2x-27.402$ where X is the absorbance and Y is the parts per billion of copper.

11. The method of claim 9 wherein, when the concentration of silver is being determined, for each 3 mL of sample, approximately 50 μL of the nitric acid solution is added, 150 μL of the buffer solution is added, and 50 μL of the indicator is added.

12. The method of claim 11 wherein: (1) the components of the indicator solution are in essentially the proportions: 0.018 g of Cadion 2B, 22.5 mL of ethanol, and 2.5 mL of Triton X-100; and (2) the components of the buffer solution are in essentially the proportions: 21 g of sodium bicarbonate and 4.2 g of sodium carbonate anhydrous made up to 250 mL with deionized water, and 0.438 g of EDTA with 1M NaOH as necessary to adjust pH to 9.2.

13. The method of claim 9 wherein, when the concentration of copper is being determined, for each 3 mL of sample, 50 μL of the nitric acid solution is added and 150 μL of the buffer/indicator solution is added.

14. The method of claim 13 wherein the components of the buffer/indicator solution are in essentially the proportions: 2 g sodium citrate dihydrate, 3 g hydroxal amine hydrochloride, and 0.03 g bathocuproine disulfonate dissolved in 25 mL of deionized water.

* * * * *